United States Patent [19]
Su et al.

[11] Patent Number: 5,155,233
[45] Date of Patent: Oct. 13, 1992

[54] INHIBITED EPOXYSILANES

[75] Inventors: Shiu-Chin Su, Croton-on-Hudson; Frederick D. Osterholtz, Pleasantville, both of N.Y.

[73] Assignee: Union Carbide Chemicals & Plastics Technology Corporation, Danbury, Conn.

[21] Appl. No.: 813,025

[22] Filed: Dec. 24, 1991

[51] Int. Cl.$^5$ ............................................. C07D 301/36
[52] U.S. Cl. ..................................... 549/202; 549/513; 549/546; 549/554; 549/555
[58] Field of Search ................ 549/202, 513, 546, 554, 549/555

[56] References Cited

U.S. PATENT DOCUMENTS

| | | | |
|---|---|---|---|
| 3,265,662 | 8/1966 | Kirwan et al. | 549/202 |
| 4,528,389 | 7/1985 | Farnham | 549/554 |
| 4,624,975 | 11/1986 | Pham | 549/202 |
| 4,632,967 | 12/1986 | Farnham | 549/554 |
| 4,822,839 | 4/1989 | Paisner | 524/239 |

FOREIGN PATENT DOCUMENTS 3639941  6/1988  Fed. Rep. of Germany ...... 549/546

OTHER PUBLICATIONS

Rychly, J. et al. "Reaction of Oxyradicals with Antioxidants on Synthetic Zeolites", *J. Polymer Science* pp. 133–143 (1973).
Vardanyan, R. et al., "Regeneration of Inhibitors in Oxidixable 1,3-Cyclohexadiene" CA77(11):74549x (1971).
Mazaletskaya, L. et al., "Mechanism of the Synergistic Action of Binary Mixtures of Antioxidants Reacting with Alkyl and Peroxyl Radicals", (1984) CA10(25)229711j.
Medvedeva, T. et al., "Oxidizability of Inhibited Lithium Greases Studied by IR Spectroscopy", CA74(24)128540w (1971).
Basaev, R., et al. "Effect of Diarylamines on the Oxidation of Isopropylbenzene", CA74(21):11131f (1971).
Romanova, L. V. et al., "Effect of Antioxidants on the Peroxide Vulvanization of Polyethylene and the Thermal Aging of the Resulting Vulcanizates", (1971) CA76(4):15333d.
Uvarova, E. M. et al., "Antioxidant Additives in Lithium.Lubricants", CA75(26):153543c (1970).
Mukhiddinov. B. F. et al., "Evaluation of the Thermostabilization of Poly(Vinyl Fluoride) by Thermogravimetric Analysis" CA102(18):150262a (1984).
Fuks, I.G. "Stability of Silica Gel Lubricants Against Oxidation" Ca74(12)55896e (1970).
Smiotanko, E. A. et al. "Process for Introducing Diphenylamine into Lithium Binders" CA73(8):37141e (1970).
Melik-Ogandzhanyan, L.F. et al.; "Photodegradation of Polychloroprene in the Presence of Diphenylamine" CA87(20)153182g (1977).
Bogdanov, M. V. et al., "Evaluation of the Efficiency of Antioxidants for Greases", CA87(20)154513c (1977).
Nikonorov, E. M. et al., "Effect of Additives on the Tribochemical Stability of Ester-Based Lubricants" CA100(22):1777411u (1984).
Koshkin, L. V. et al. "Antioxidative Effectiveness of Secondary Aromatic Amines in the Oxidation of Rubber" CA104(4):20534w (1985).
Grigor'ev. V. V. et al., "Stability of Low-Molecular--Weight Polybutenes Under Ocidative Thermal and Electric Exposures" CA105(22):192047b (1986).

*Primary Examiner*—Joseph E. Evans
*Attorney, Agent, or Firm*—Bonnie L. Deppenbrock

[57] ABSTRACT

Compositions are provided containing epoxysilanes and diphenylamine in an amount at least sufficient to inhibit degradation. Methods for producing such compositions are also provided.

15 Claims, No Drawings

INHIBITED EPOXYSILANES

FIELD OF THE INVENTION

This invention relates to epoxysilanes having enhanced stability towards degradation prior to end use application. This invention also relates to stabilization of such compounds during their initial formation, purification and storage.

BACKGROUND OF THE INVENTION

Epoxysilanes are chemically reactive materials which are useful in various commercial applications. For example, such compounds are useful as coupling agents. In particular, 3-glycidoxypropyltrimethoxysilane is widely used as an additive in epoxy resins used in the manufacture of circuit boards. This particular compound has the formula $$H_2C\underset{O}{\underset{\diagdown\diagup}{-}}CH-CH_2-O-CH_2CH_2CH_2-Si(OCH_3)_3 \quad (A)$$

and is sometimes referred to herein for brevity as "GPTMS".

Epoxysilanes are prepared by the known reaction of organosilicon compounds having an Si—H functional group and an epoxy-containing compound. For example, GPTMS is prepared by reacting allyl glycidyl ether and trimethoxysilane. Although the resulting product is chemically stable, it can over time undergo degradation resulting in the formation of various ionic by-products. These by-products include formate, acetate and glycolate ions, which are undesirable in the product In critical, high purity applications, commonly encountered in the electronics industry, these ionic impurities may render the product unusable for its intended purpose.

The degradation of epoxysilanes is a function of many variables, such as time, oxygen content and temperature. Improperly inhibited material may be acceptable for a particular application initially, but over time, the level of impurities increases rendering the material unusable. The continuous degradation of the material results in increased testing costs to determine if the silane is still acceptable or in increased off-specification production if an unacceptable epoxysilane is used.

Currently, nitrogen blankets are employed to prevent the degradation of epoxysilanes. The shortcomings of this technique include the need for an available nitrogen source and the cost of the nitrogen. Further, when only relatively small quantities of epoxysilanes are used, such as can be supplied from fifty-five gallon supply drums, replacing the nitrogen blanket after the necessary amount of epoxysilane is removed is often impractical.

Accordingly, a need exists to stabilize epoxysilanes against degradation with an inhibitor which is capable of inhibiting the degradation and which does not require special process features to be effective. It is also desirable that the inhibitor not adversely affect the properties of the product.

SUMMARY OF THE INVENTION

The present invention provides epoxysilanes compositions stabilized with diphenylamine. The compositions are stable against degradation. The present invention also provides a method for stabilizing epoxysilanes by providing to the silane diphenylamine in an amount at least sufficient to inhibit degradation of the silane.

DETAILED DESCRIPTION OF THE INVENTION

Diphenylamine is a well known compound and has the formula, $C_6H_5-NH-C_6H_5$. It is commercially available from Sigma Chemical Company, Inc.

The epoxysilanes which are stabilized with diphenylamine as described herein are encompassed by the following Formula I:

$$R(OR^1)_a(R^2)_bCH_2CH_2\underset{\underset{R_n^3}{|}}{Si}(OR^4)_{(3-n)} \quad (I)$$

where R, $R^1$, $R^2$, $R^3$, $R^4$, a, b and n are defined hereinbelow.

In Formula I, R is an epoxy-containing group having from 3 to 6 carbon atoms and in which the carbon atoms of the epoxy moiety $$HC\underset{|}{\underset{\diagdown\diagup}{\overset{O}{-}}}CH.$$

can be part of a linear or cyclic structure. For example, the remaining valences of the epoxy group can be satisfied by bonds to hydrogen or acyclic carbon as in $$H_2C\underset{}{\underset{\diagdown\diagup}{\overset{O}{-}}}CH-CH_2-.$$

Alternatively, the remaining valences of the epoxy group can be satisfied by bonds to ring carbon atoms of a cycloalkyl group such as, in particular, the 1,2-epoxycyclohexyl group, Further with respect to Formula I, $R^1$ is an alkylene group of one to four carbon atoms, and $R^2$ is an alkylene group of one to eight carbon atoms. The $R^1$ and $R^2$ groups may be linear or branched and any combination of such groups can be present. The divalent $R^1$ group is exemplified by methylene ($-CH_2-$), ethylene ($-CH_2CH_2-$) and higher homologous groups such as propylene, isopropylene and butylene. $R^2$ can be any such alkylene groups and in addition can be $C_5-C_8$ alkylene groups such as, for example, isopentylene.

$R^3$ of Formula I is a monovalent hydrocarbon group having from 1 to 10 carbon atoms. The $R^3$ groups include alkyl, aryl and aralkyl groups as illustrated by methyl, ethyl, butyl, hexyl, phenyl and benzyl. Of these, the lower ($C_1-C_4$) alkyls are preferred. Usually $R^3$ is methyl.

In Formula I, $R^4$ can be alkyl, alkoxy-substituted alkyl or a trialkylsilyl group, wherein each of said alkyl and alkoxy groups can have from one to eight carbon atoms. In addition, $R^4$ can be an alkenyl group having from two to eight carbon atoms. The $R^4$ groups can be linear or branched and may be the same as or different from one another. Accordingly, illustrative of the Si-bonded $OR^4$ groups are methoxy, ethoxy, isopropoxy, beta-methoxyethoxy, isopropenyloxy, and trimethylsilyloxy groups.

In further reference to Formula I, n is 0, 1 or 2, each of a and b can have a value of zero or one, and the sum $a \pm b$ can be zero, one or two.

Illustrative of such epoxysilanes which are stabilized as described herein are:
3-glycidoxypropyltrimethoxysilane,
3-glycidoxypropyltriethoxysilane,
3-glycidoxypropyltripropoxysilane,
3-glycidoxypropyltri(2-methoxyethoxy)silane,
3-glycidoxypropyldimethoxymethylsilane,
3-glycidoxypropyldiethoxymethylsilane,
3-glycidoxypropyldibutoxymethylsilane,
3-glycidoxypropyldimethylmethoxysilane,
3-glycidoxypropyldimethylpropoxysilane,
5,6-epoxyhexyltrimethoxysilane,
5,6-epoxyhexyltriethoxysilane,
beta-(3,4-epoxycyclohexyl)ethyltrimethoxysilane,
3-glycidoxypropylbis(trimethylsiloxy)methylsilane,
3-glycidoxypropylmethyl-di-isopropenoxysilane,
3-glycidoxypropylpentamethyldisiloxane, and the like.

The above-described epoxysilanes are prepared by methods known to the art; see, for example, U.S. Pat. No. 2,823,218. For example, epoxysilanes encompassed by Formula I can be prepared by the reaction of an Si—H functional compound with an epoxy compound having an ethylenically unsaturated group, as shown by the following Equation 1:

$$R(OR^1)_a(R^2)_bCH=CH_2 + HSi(OR^4)_{(3-n)} \overset{R_n^3}{\longrightarrow} \quad (1)$$

$$R(OR^1)_a(R^2)_bCH_2CH_2\overset{R_n^3}{\underset{|}{Si}}(OR^4)_{(3-n)}$$

where R, $R^1$, $R^2$, $R^3$, $R^4$, a, b and n are as defined above with respect to Formula I. The hydrosilation reactions encompassed by Equation 1 are usually conducted in the presence of a platinum-containing catalyst, such as chloroplatinic acid. The reaction is normally effected at a temperature from about 50 to about 200° C. The resulting reaction product is usually purified, typically by distilling the product at its boiling point at reduced pressures of about 1–50 mm Hg.

By way of illustrating the reactions encompassed by Equation 1, the reaction of 1,2-epoxy-4-vinylcyclohexane with trimethoxysilane provides beta-(3,4-epoxycyclohexyl)ethyltrimethoxysilane, that is, the epoxysilane having Formula I wherein R is 1,2-epoxycyclohexyl,

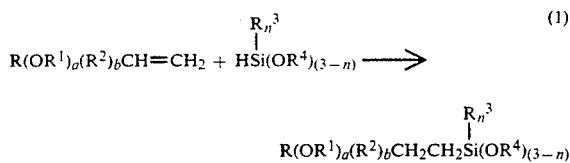

a, b and n are zero, and $R^4$ is methyl. Further, when the ethylenically unsaturated reactant is allyl glycidyl ether and the silane reactant is trimethoxysilane, the hydrosilation reaction of Equation 1 provides 3-glycidoxypropyltrimethoxysilane (GPTMS); that is, the epoxysilane of Formula I wherein

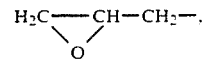

$R^1$ is —CH—$_2$—, $R^4$ is —CH$_3$, a is one, b is zero and n is zero.

In accordance with the teachings of the present invention, diphenylamine can be added to any step in the process by which the epoxysilane is produced. The inhibitor may be provided to the process of this invention by adding it as a separate stream directly to the zone in which the epoxysilane is to be initially formed or purified. Alternatively, the inhibitor can be provided to the zone as a component of one or more of the reactant streams or of the mixture to be distilled. In a preferred embodiment, diphenylamine is provided to the epoxysilane after distillation, prior to packaging, storage and shipping of the final product for end use application. It is to be understood that the diphenylamine inhibitor may be provided to any step of a batch or continuous process without departing from the scope of this invention.

The stabilization of the epoxysilane is effected by employing the diphenylamine inhibitor in an amount at least sufficient to inhibit degradation. The particular minimal amount used depends largely on the amount of oxygen and temperature to which the silane is exposed. Generally, higher oxygen levels and higher temperatures promote degradation of the silane.

Typically, from about 1 to about 1,000 ppm (parts by weight per million parts by weight of silane) of diphenylamine is sufficient to inhibit degradation of the silane. In a preferred embodiment 5–100 ppm of diphenylamine is employed.

Included within the scope of the present invention is the use of diphenylamine in combination with other inhibitors. Illustrative of such other inhibitors are: bisphenol A, Ethanox® 322, Ethanox® 703, Ionol® and Agerite White ™, including mixtures thereof. Diphenylamine is present in such combinations in an amount sufficient to provide an inhibitor system having improved performance relative to said other inhibitors or mixtures of said other inhibitors not containing diphenylamine. Additional inhibitors and other additives may also be included for their effects on other aspects of the process or products which incorporate the epoxysilane without departing from the scope of the present invention.

The inhibitor is typically provided to the epoxysilane-forming reaction or purification process as a solution. This technique provides more uniform distribution of the inhibitor throughout the medium to be stabilized. Any solvent of diphenylamine may be used provided the solvent does not adversely affect product quality or process control. Typically, the solvents selected are aromatic hydrocarbons well known in the art. These solvents include toluene, benzene and xylene, with toluene being preferred.

The effectiveness of the inhibitor can be determined over time by measuring the concentration of ionic species within the silane. Without being limited to the following explanation, it is presumed that the ionic species arise from the oxidation of the epoxysilane. Epoxysilanes typically contain less than 10 ppm of anionic contaminants when manufactured. The anion level increases over time as oxidative degradation occurs. Illustrative anions formed by the degradation process include formate, acetate and glycolate anions. Measurement of these contaminants is typically performed by ion chromatography, a technique well known in the art.

The Examples which follow are presented for the purpose of illustrating the invention and are not to be construed as unduly limiting the claims. All parts and percentages are by weight unless otherwise specified.

DEFINITIONS

The following designations used in the Examples and elsewhere herein have the meaning set forth below.

In each formula showing a —C₄H₉ group, it is to be understood that the group is tertiary butyl.

|  | Supplier |
|---|---|
| Agerite White TM<br>N,N'-Di-beta-naphthyl-p-phenylenediamine | R. T. Vanderbilt Co., Inc. |

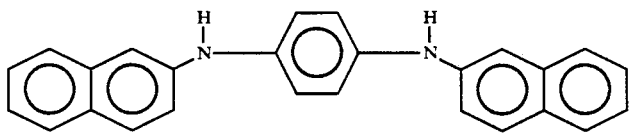

| Bisphenol A | Aldrich Chemical Co., Inc. |
|---|---|

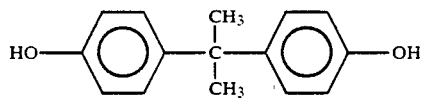

| Ethanox ® 322 | Ethyl Corp. |
|---|---|

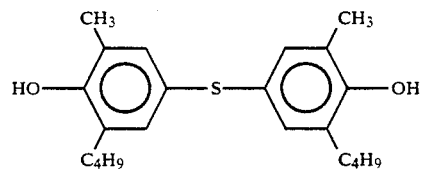

| Ethanox ® 703 | Ethyl Corp. |
|---|---|

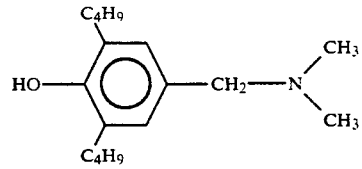

| Ionol ® | Aldrich Chemical Co., Inc. |
|---|---|

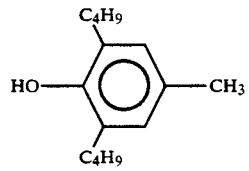

| Irganox ® 245 | Ciba Geigy Corp. |
|---|---|

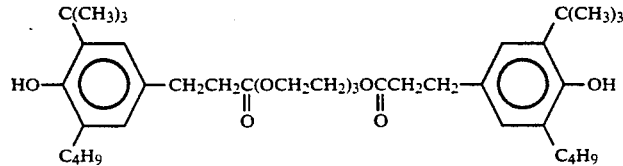

| Irganox ® 565 | Ciba-Geigy Corp. |
|---|---|

-continued
Supplier
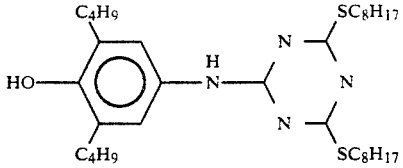
Irganox ® 1010      Ciba Geigy Corp.
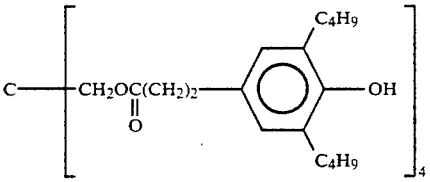
Irganox ® 1035      Ciba-Geigy Corp.
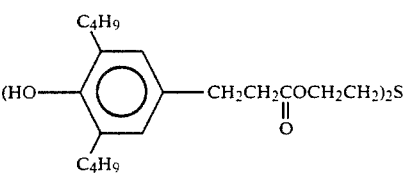
Irganox ® 1076      Ciba-Geigy Corp.
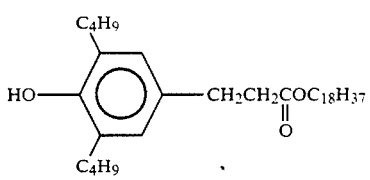
Irganox ® 3114      Ciba-Geigy Corp.
Tris(3,5-di-tert-butyl-4-hydroxybenzyl)isocyanurate
Irganox ® B-225      Ciba-Geigy Corp.
1/1 Blend of tris-(2,4-di-t-butylphenyl)phosphate
and Irganox 1010
Naugard ® 445      Uniroyal Chemical Co., Inc.
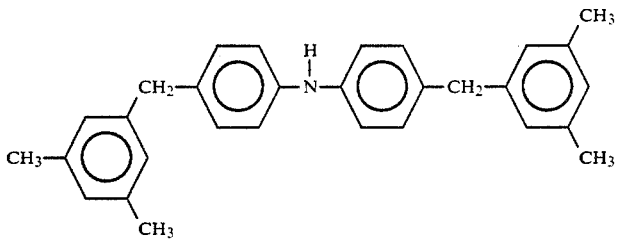
Diphenylamine      Sigma Chemical Co., Inc.
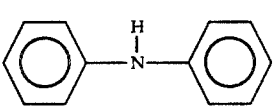
Phloroglucide      Ishihara Sango
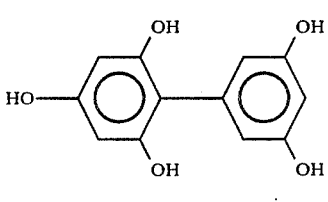

| | Supplier |
|---|---|
| Propylgallate | Aldrich Chemical Co., Inc. |

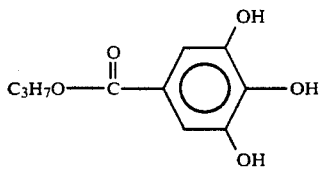

EXAMPLE 1

Samples of 3-glycidoxypropyltrimethoxysilane (GPTMS) were placed in brown sample bottles in the presence of various inhibitors, nitrogen and/or air. One bottle (Sample A) was filled to the brim with GPTMS while under a nitrogen atmosphere. A second bottle (Sample B) was half-filled with GPTMS under air. The remaining bottles (Samples C-R) were half-filled with GPTMS under air to which 50 ppm of the respective inhibitors were added. The brown sample bottles were stored for 130 days at 60° C. Ion chromatography was performed on the samples to determine the level of ionic species present. The results are presented below. The anion concentration listed in the last column is the total anion concentration calculated as if all anion species found are formate ions.

| Sample | Inhibitor | Ion Concentration (in ppm) | | | Total anion concentration as ppm Formate |
|---|---|---|---|---|---|
| | | Acetate | Glycolate | Formate | |
| R | Diphenylamine | 5.06 | 1.49 | 16.39 | 21.14 |
| A | None nitrogen | 7.13 | 1.72 | 28.39 | 34.86 |
| I | Agerite White | 10.39 | 1.5 | 28.65 | 37.47 |
| H | Naugard 445 | 14.51 | 2.14 | 36.38 | 48.73 |
| P | Ethanox 703 | 11.27 | 3.11 | 38.29 | 48.75 |
| N | Irganox 1035 | 12.84 | 2.72 | 38.54 | 49.97 |
| L | Irganox 1010 | 13.89 | 2.88 | 44.08 | 56.4 |
| C | Phloroglucide | 13.00 | 4.16 | 46.32 | 58.73 |
| K | Bisphenol A | 13.3 | 3.64 | 47.82 | 60.15 |
| Q | Irganox 245 | 15.48 | 2.86 | 52.45 | 65.97 |
| E | Irganox 3114 | 10.99 | 3.3 | 56.03 | 66.39 |
| G | Irganox 565 | 21.15 | 4.59 | 50.35 | 69.24 |
| F | Irganox 1076 | 12.27 | 3.98 | 59.73 | 71.48 |
| M | Irganox B-225 | 13.16 | 3.17 | 60.13 | 72.07 |
| O | Ethanox 322 | 13.66 | 4.02 | 59.42 | 72.25 |
| J | Ionol | 21.38 | 2.39 | 63.55 | 81.29 |
| B | None air | 18.21 | 2.76 | 70.94 | 86.48 |
| D | Propylgallate | 11.91 | 3.32 | 81.16 | 92.24 |

The above results demonstrate the surprising effectiveness of diphenylamine in preventing degradation of GPTMS. Diphenylanine was the only inhibitor which minimized formation of anions more effectively than nitrogen. Also especially noteworthy is that GPTMS inhibited with diphenylamine contained substantially fewer anions than GPTMS inhibited with either Agerite White (Sample I) or Naugard 445 (Sample H), both of which are structurally similar to diphenylamine in that they are also aromatically unsaturated amines.

We claim:

1. A stable composition comprising an epoxysilane and diphenylamine in an amount at least sufficient to inhibit degradation of the silane.

2. The composition of claim 1 wherein diphenylamine is present in an amount from 1 to 1000 ppm based on the weight of the silane.

3. The composition of claim 1 wherein diphenylamine is present in an amount from 5 to 100 ppm based on the weight of the silane.

4. The composition of claim 1 which additionally contains at least one other degradation inhibitor.

5. The composition of claim 1 wherein the epoxysilane has the formula:

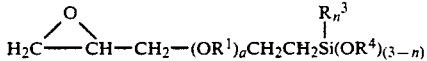

where
R$^1$ is an alkylene group having from one to four carbon atoms;
R$^3$ is a monovalent hydrocarbon group having from one to ten carbon atoms;
a has a value of zero or one;
R$^4$ is an alkyl, alkoxy-substituted alkyl or a trialkylsilyl group, each of said alkyl and alkoxy groups having from one to eight carbon atoms, or an alkenyl group having from two to eight carbon atoms; and
n has a value of zero, one or two.

6. The composition of claim 1 wherein the epoxysilane has the formula

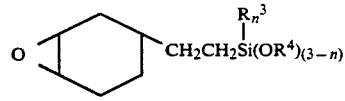

where:
R$^3$ is a monovalent hydrocarbon group having from one to ten carbon atoms;
R$^4$ is an alkyl, alkoxy-substituted alkyl or a trialkylsilyl group, each of said alkyl and alkoxy groups having from one to eight carbon atoms, or an alkenyl group having from two to eight carbon atoms; and
n has a value of zero, one or two.

7. The composition of claim 6 wherein R$^4$ is methoxy and n is zero.

8. The process of producing epoxysilanes which comprises providing to the epoxysilane-forming reaction mixture diphenylamine in an amount at least sufficient to inhibit degradation of the epoxysilane.

9. The process of claim 8 wherein diphenylamine is provided in an amount from 1 to 1000 ppm based on the weight of the silane.

10. The process of claim 8 wherein the epoxysilane has the formula

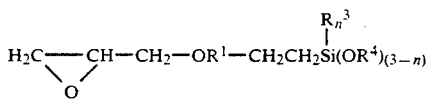

where:
R$^1$ is an alkylene group having from one to four carbon atoms;
R$^3$ is a monovalent hydrocarbon group having from one to ten carbon atoms;
R$^4$ is an alkyl, alkoxy-substituted alkyl or a trialkylsilyl group, each of said alkyl and alkoxy groups having from one to eight carbon atoms, or an alkenyl group having from two to eight carbon atoms; and
n has a value of zero, one or two.

11. The process of claim 10 wherein the epoxysilane is 3-glycidoxypropyltrimethoxysilane.

12. The process of distilling an epoxysilane from a mixture containing same which comprises providing diphenylamine to the overhead product in an amount at least sufficient to inhibit degradation of the silane.

13. The process of claim 12 wherein the distillation is conducted at subatmospheric pressure.

14. The process of claim 12 wherein the epoxysilane is 3-glycidoxypropyltrimethoxysilane.

15. The process of claim 12 wherein the epoxysilane is beta-(3,4-epoxycyclohexyl)ethyltrimethoxysilane.

* * * * *